(12) United States Patent
Paturle et al.

(10) Patent No.: US 10,365,248 B2
(45) Date of Patent: Jul. 30, 2019

(54) METHOD FOR ACOUSTIC DETECTION OF THE CONDITION OF THE ROAD AND THE TIRE

(71) Applicants: Antoine Paturle, Clermont-ferrand (FR); Jérôme Antoni, Clermont-ferrand (FR)

(72) Inventors: Antoine Paturle, Clermont-ferrand (FR); Jérôme Antoni, Clermont-ferrand (FR)

(73) Assignee: Compagnie Generale des Establissements Michelin, Clermont-Ferrand (FR)

( * ) Notice: Subject to any disclaimer, the term of this patent is extended or adjusted under 35 U.S.C. 154(b) by 362 days.

(21) Appl. No.: 15/103,987

(22) PCT Filed: Dec. 15, 2014

(86) PCT No.: PCT/FR2014/053352
§ 371 (c)(1),
(2) Date: Jun. 13, 2016

(87) PCT Pub. No.: WO2015/092253
PCT Pub. Date: Jun. 25, 2015

(65) Prior Publication Data
US 2016/0349219 A1 Dec. 1, 2016

(30) Foreign Application Priority Data
Dec. 18, 2013 (FR) ...................................... 13 62879

(51) Int. Cl.
*G01N 29/14* (2006.01)
*B60C 23/00* (2006.01)
(Continued)

(52) U.S. Cl.
CPC ............. *G01N 29/14* (2013.01); *B60C 23/00* (2013.01); *B60C 23/06* (2013.01);
(Continued)

(58) Field of Classification Search
CPC ............... G01N 29/14; G01N 29/4427; G01N 29/4445; G01N 29/4472; G01N 29/46;
(Continued)

(56) References Cited

U.S. PATENT DOCUMENTS

| | | | |
|---|---|---|---|
| 5,436,612 A | * | 7/1995 | Aduddell ................. B60Q 1/52 340/438 |
| 5,586,028 A | | 12/1996 | Sekine et al. .......... 364/423.098 |

(Continued)

FOREIGN PATENT DOCUMENTS

| | | |
|---|---|---|
| EP | 2 573 594 A1 | 3/2013 |
| JP | 2008-143508 A | 6/2008 |

OTHER PUBLICATIONS

International Search Report dated Apr. 17, 2015, issued by WIPO in connection with International Application No. PCT/FR2014/053352.

*Primary Examiner* — Marrit Eyassu
(74) *Attorney, Agent, or Firm* — Venable LLP

(57) ABSTRACT

In a method for determining conditions of a road and a tire, a measurement of a sound signal produced by the tire running on the road during a timeframe is recorded, and a spectral density of a power of the sound signal over a frequency interval is determined. The frequency interval is segmented into frequency bands, and each frequency band is associated with a representative data element representing a mean acoustic power measured in the frequency band. The representative data elements obtained from the measurement form variables of a vector associated with the measurement. A road condition and a tire condition are determined via a (Continued)

discriminant analysis of the representative data elements using a learning base. Each representative data element is obtained by finding a ratio between a mean acoustic power measured in a corresponding frequency band and a total acoustic power measured over an entirety of the frequency interval.

15 Claims, 4 Drawing Sheets

(51) Int. Cl.
    *G01N 29/44*     (2006.01)
    *G01N 29/46*     (2006.01)
    *B60C 23/06*     (2006.01)
    *G01M 17/02*     (2006.01)
    *G01H 3/00*     (2006.01)

(52) U.S. Cl.
    CPC ...... *G01M 17/025* (2013.01); *G01N 29/4427* (2013.01); *G01N 29/4445* (2013.01); *G01N 29/4472* (2013.01); *G01N 29/46* (2013.01); *B60T 2210/10* (2013.01); *G01H 3/00* (2013.01); *G01N 2291/2692* (2013.01)

(58) Field of Classification Search
    CPC ............ G01N 2291/2692; B60C 23/00; B60C 23/06; G01M 17/025; B60T 2210/10; G01H 3/00
    USPC .............................................................. 73/8
    See application file for complete search history.

(56) References Cited

U.S. PATENT DOCUMENTS

| | | | |
|---|---|---|---|
| 8,731,767 B2 | 5/2014 | Paturle | 701/31.4 |
| 8,833,410 B2 | 9/2014 | Paturle | 152/154.2 |
| 8,881,573 B2 | 11/2014 | Paturle et al. | 73/8 |
| 8,892,298 B2 | 11/2014 | Paturle et al. | B60C 11/246 |
| 8,904,869 B2 | 12/2014 | Paturle | 73/584 |
| 2004/0212516 A1* | 10/2004 | Bhagavathula | B60R 16/0237 340/901 |
| 2005/0076987 A1* | 4/2005 | O'Brien | B60C 23/06 152/415 |
| 2008/0018441 A1* | 1/2008 | Orrell | B60C 23/06 340/438 |
| 2009/0271061 A1* | 10/2009 | Wang | G01M 17/06 701/29.5 |
| 2011/0252862 A1* | 10/2011 | Paturle | B60C 11/24 73/8 |
| 2012/0266650 A1 | 10/2012 | Paturle | 73/8 |
| 2012/0273102 A1 | 11/2012 | Paturle | 152/154.2 |
| 2014/0121997 A1 | 5/2014 | Paturle | 702/34 |
| 2014/0124108 A1 | 5/2014 | Paturle | 152/154.2 |
| 2014/0130948 A1 | 5/2014 | Paturle | 152/154.2 |
| 2014/0174613 A1 | 6/2014 | Paturle et al. | 152/154.2 |
| 2015/0321522 A1 | 11/2015 | Paturle | B60C 11/24 |

* cited by examiner

METHOD FOR ACOUSTIC DETECTION OF THE CONDITION OF THE ROAD AND THE TIRE

FIELD OF THE INVENTION

The invention relates to a method for detecting the condition of the road and the tire fitted to a vehicle travelling on this road, on the basis of the noise generated by the tire when it comes into contact with the ground.

RELATED ART

It is useful to know the condition of the road or the tire at every instant, in order to interact with the driver or with the driver assistance systems, so that they can be informed in real time of the variation in the running conditions, and more generally of the possible modification of the conditions of the grip of the tire and the handling of the vehicle.

The aim of these methods is therefore to indicate the variation of meteorological conditions, such as changes between conditions of running on dry, moist, wet or snow-covered ground. They are based on the finding that the frequency and intensity of sound generated by the tire vary when the road condition changes, and they analyse sound recordings made by microphones positioned close to the tire and the road.

The meteorological condition of the road is determined from the recording of a frequency spectrum of acoustic power, by using carefully chosen ratios, or by comparing this spectrum with pre-recorded data.

However, it has been found that the accuracy and reliability of all these methods is largely dependent on the introduction of supplementary parameters such as a knowledge of the running speed, the temperature or the loading of the vehicle, the degree of wear or the type of tread pattern used, or, in the most complex methods, a recording of the visual condition of the road in front of the vehicle. It is therefore necessary to combine data obtained from a plurality of sensors, and this has some effect on the cost of the use of the proposed devices.

BRIEF DESCRIPTION OF EMBODIMENTS OF THE INVENTION

The object of the invention is to provide a robust solution to the problem of determining the meteorological condition of the road. At the same time, the method proposed by the invention can also be used, most unexpectedly, to determine, on the sole basis of a sound recording, other parameters such as the type of surfacing, the degree of wear of the tire, or the type of tread pattern used.

The sound recordings are made using a microphone carefully positioned on the vehicle. The spectral density of the acoustic power is distributed over a given frequency interval. This spectrum varies as a function of a set of modalities such as the meteorological conditions, the condition of the road, the degree of wear of the tire, the type of tread pattern of the tire, and, to a lesser extent, the inflation pressure, the load, etc. One of the major modalities that may modify this spectrum, all other conditions being equal, is the speed of the vehicle at the moment when the measurement is made.

It has been demonstrated that this variation can be practically neutralized if, instead of considering the power spectrum based on the measurement, the spectrum is recalculated by "normalizing" the measured data, using the total acoustic power recorded during the measurement time over the whole frequency interval. The aim of this is to eliminate the speed effect and substantially prevent the variation of the measurement by this modality.

The object of the invention is to take advantage of this finding.

The method of determining the condition of a road and the condition of a tire fitted on a vehicle travelling on said road according to the invention therefore comprises the steps in which:

a measurement of a sound signal produced by the tire running on a surface of the road during a given time frame is recorded, a spectral density of the power of the sound signal over a given frequency interval is determined, the frequency interval is segmented into a plurality of frequency bands of pre-determined width, and each frequency band is associated with a data element representing a mean acoustic power measured in said frequency band, the representative data obtained from a measurement forming variables of a vector associated with said measurement, a condition of the road and of the tire corresponding to the vector associated with the completed measurement is determined, by means of a discriminant analysis of the data using a learning base composed of a set of vectors associated with previously recorded measurements which have been made, by the same steps as those above, in known running conditions according to modalities which each represent a given condition of the road and the tire.

The method is characterized in that the representative data forming the variables of a vector associated with a measurement are obtained by finding the ratio between the mean acoustic power measured in a frequency band and the total acoustic power measured over the whole frequency interval.

Thus it is now possible to obtain reliable information on the condition of the road and, as will also be demonstrated, on the condition of the tire, without any need to allow for the speed, on the basis of a single acoustic measurement and without the need to introduce supplementary parameters to interpret the measurement.

The method according to the invention may also have the following characteristics, separately or in combination:

The total measured acoustic power is equal to the sum of the mean acoustic powers of all the frequency bands of the frequency interval concerned.

The frequency bands are determined by dividing the frequency interval into thirds of an octave.

The time frame of a measurement is less than or equal to 0.5 seconds, and preferably less than or equal to 0.25 seconds.

The frequency interval is in the range from 0 Hz to 20 kHz.

The frequency interval is in the range from 200 Hz to 20 kHz.

A class of "weather" modalities, composed of different meteorological conditions of the road, comprises a dry condition, a moist condition and a wet condition.

A class of "surface condition" modalities, composed of different conditions of the road surface, comprises a closed condition, a medium condition and an open condition.

A class of "wear" modalities, composed of different conditions of wear of the tire, comprises a new condition, a half-worn condition and a worn condition.

A class of "tread pattern" modalities, composed of different types of tire tread pattern, comprises a summer pattern and a winter pattern.

The discriminant analysis of the data includes steps in which:
- a reduced discriminant space is determined, using the learning base, and areas formed by each modality or combination of modalities are identified in this space,
- the vector associated with a measurement is transformed in said reduced discriminant space, and, on the basis of the location of said vector, a probability is associated with the measurement according to each of the modalities or combinations of modalities,
- the most probable modality is determined according to each of the classes of modalities.

A modality according to the "surface condition" "wear", or "tread pattern" modality is associated with the measurement, after it has previously been determined that the measurement was made on a dry road.

A probability is associated with the measurement according to each of the combinations of modalities containing this modality, and the modality of the class having the highest probability is attributed to this measurement.

A diagnosis of the condition of the tire is made according to the "wear" modality or the "tread pattern" modality, by combining the results of measurements made in different time intervals.

The sound signal generated by the tire is measured by means of a microphone placed in the front part of a wheel housing located at the rear of the vehicle.

BRIEF DESCRIPTION OF THE DRAWINGS

The invention will be more easily understood from a perusal of the attached drawings, which are provided by way of example and are not in any way limiting, and in which.

DETAILED DESCRIPTION OF EMBODIMENTS OF THE INVENTION

Figure 1:
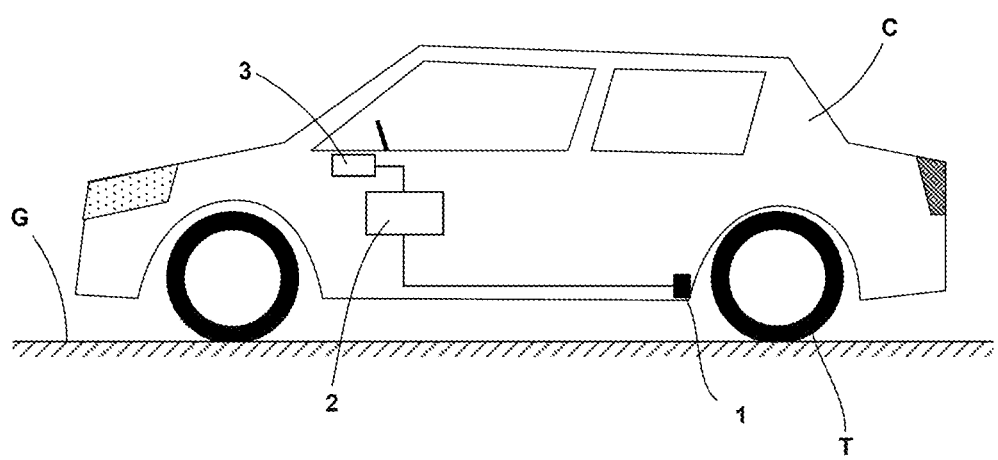
FIG. 1 shows a vehicle fitted with a device for measuring and analysing the acoustic power of a tire.

The vehicle C running on a ground G, shown schematically in FIG. 1, comprises front and rear wheel housings in which wheels fitted with tires T are housed.

When the vehicle C moves, the tire T generates a noise whose amplitude and frequency depend on multiple factors. This sound pressure is in fact the superimposition of noises from various sources such as noises generated by the contact of the tread elements with the ground G, by the movements of air between the tread elements, by the water particles lifted by the tire, or the air flows related to the speed of the vehicle. These noises are received with the superimposition of noises related to the environment of the vehicle, such as the engine noise. All these noises are also dependent on the speed of the vehicle.

A receiving means such as a microphone 1 is fitted in a wheel housing to receive the running noises as closely as possible to the place where they are generated. Evidently, practical precautions must be taken to protect the microphone from external attack by water or mud splashes, grit or other factors. The microphone is therefore preferably fitted at the front of the wheel housing.

Ideally, it is considered that the best way of capturing all the running noises generated by the tires is to fit a microphone in each of the wheel housings. However, a single microphone is sufficient to determine the road condition (the meteorological condition and the surface porosity). In the latter case, it is preferable to isolate the aerodynamic and engine noises.

Fitting the microphone in the front part of one of the rear axle wheel housings appears to be a good option.

The microphone can also be placed in the rear bumper, or in the front bumper.

The vehicle also comprises a computer 2, connected to the microphone, and configured to execute operations for formatting and analysing, as detailed below, the raw information obtained from the microphone, and for estimating the condition of the ground or the tire on the basis of a measurement of the acoustic power detected by the microphone.

Information storage means are associated with the computer. These means can be used to store in memory the data relating to a learning plan concerning measurements made in known running conditions and according to modalities describing different states of the road or tire.

Finally, the data relating to the condition of the road or the tire can be transmitted to display means or to driver assistance systems 3, or to a remote server.

The term "modality" is here taken to mean a set of conditions related to the condition of the ground or the tire, which may cause a substantial variation in the measurement of the sound pressure.

As mentioned above, the number of parameters having a potential effect on the noise of the tire may be large. However, it appears that some parameters have a weak or second-order effect on the nature of the noise generated by the tire. This may be the case, for example, with the internal pressure of the tire or the load on the tire.

Surprisingly, it appears that the meteorological condition of the road is a first-order parameter. Its effect on the tire noise is very considerable, and, above all, it is independent of any other parameters such as the condition of the road surface, the condition of wear of the tire, or the type of tread pattern of the tire. These other parameters are also capable, to a lesser degree, of causing variations in the running noise, to the extent that it is possible to discern their specific acoustic signatures.

The meteorological condition of the road forms a first class of modalities, called the "weather" class, in which a dry road can be distinguished from a moist road, characterized by a water level flush with the natural roughnesses of the road surface, or a wet road, for which the water level exceeds the level of the natural roughnesses of the road surface. A real-time knowledge of the variation of the meteorological conditions of the road is of primary importance for the adaptation of driver assistance systems, for example.

In a second class of modalities, called the "surface condition" class, different conditions of the road surface can also be distinguished. A surface is described as a closed surface if it has a smooth appearance, without roughness, as in the case of bitumen that has sweated out after being subjected to high heat. A surface is considered to be open if the roughnesses are substantial, such as those of a worn surface or of a country road repaired rapidly using a surface dressing formed by spraying chippings on to bitumen. A medium surface describes any surface in an intermediate condition between the two preceding conditions, and is applied more particularly to new surfaces. It is assumed here that the porosity of the surface affects the sound permeability or reflection of the noise generated by the tire. This is because the phenomenon of pumping the air trapped between the ground and the tire tread pattern, as well as the phenomenon of amplification of the noise by the air wedge formed by the curvature of the tire and the ground, become more pronounced as the road surface becomes more closed. A real-time knowledge of the condition of a road may prove useful in the case where, for example, this information is returned by a large number of vehicles or a dedicated vehicle fleet to a central monitoring and maintenance system of the road network.

Regarding the condition of the tire, the wear condition can be recognized by distinguishing the new condition, the used condition, and an intermediate condition considered here as the condition of the half-worn tire, within a third class of modalities, called the "wear" class. Information on the variation of the wear characteristic over time is also essential, especially if it is combined with the information on the meteorological condition of the road. This is because it is known that a vehicle fitted with worn tires running on a wet surface is more likely to lose its grip ("aquaplaning") than if it had new tires.

Finally, the method according to the invention can discern a fourth class of modalities, called the "tread pattern" class and relating to the type of tread pattern on the tire, distinguishing whether it is a summer or a winter tread pattern. These two types of tires are essentially distinguished by treads having different tread patterns, which are highly incised with multiple sipes in the case of winter tread patterns, or more directional and less incised in the case of summer tread patterns, as well as by the nature of the materials forming the tread, which are softer in winter tires and harder in summer tires. These characteristics have a certain effect on the behaviour and handling of the vehicle, and may constitute useful information for adapting the driving system, particularly in regions where tire fittings change between summer and winter periods.

The method according to the invention enables each of these different classes of modalities to be highlighted in an isolated manner, more particularly in the case of the weather characteristic, or in a combined manner for the other characteristics.

Figure 2:
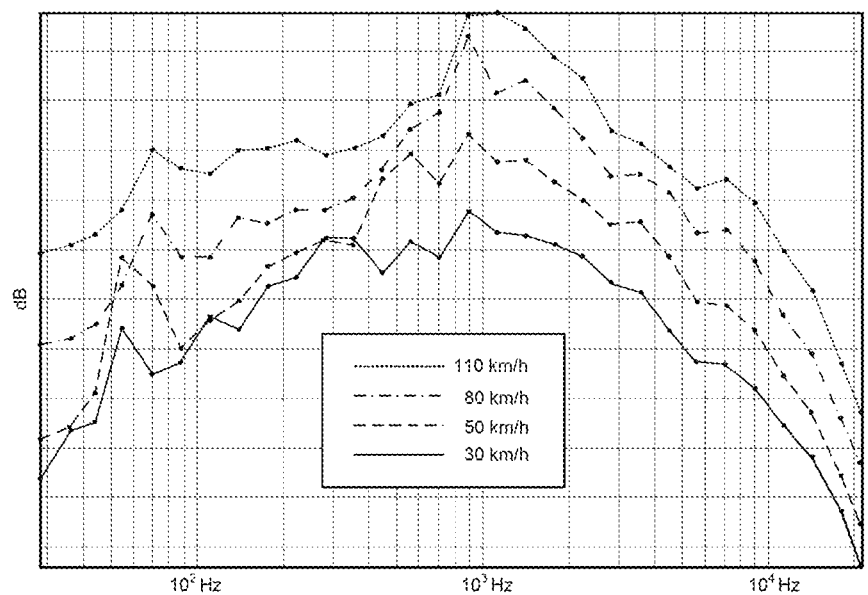
FIG. 2 shows a non-normalized acoustic power spectrum for measurements made at different speeds.

FIG. 2 is a spectral representation of the acoustic power recorded by the microphone during a time frame. The term "time frame" is here taken to mean the time interval, usually short, during which a recording is made, the data used as the basis for a measurement being established from this recording. This time frame of a measurement is less than or equal to 0.5 seconds, or ideally less than or equal to 0.25 seconds.

This spectral representation represents the received acoustic power (in dB) as a function of the frequency, over a given frequency interval, typically the audible frequency interval in this case, lying between 0 Hz and 20 kHz.

More specifically, the spectral representation of FIG. 2 is obtained by breaking down the frequency interval into frequency bands of predetermined widths, and by assigning to each frequency band a characteristic value equal to the mean power measured in this frequency band. A division of the frequency interval by bands of one third of an octave appears most appropriate. Thus each point on each of the curves of FIG. 2 represents a mean acoustic power for a given frequency band, measured during a time frame in the running conditions in which, all other things being equal, only the speed is varied (typically from 30 km/h to 110 km/h).

It is then found that the curves representing the spectral powers are offset from one another, and that the total dissipated acoustic power increases as a function of speed. However, the general form of the curves remains the same.

This finding is repeated when one or more modalities of the other classes of is changed and the resulting curves are compared while varying only the speed parameter.

The total acoustic power is then determined over the whole frequency interval, which may be considered to be the surface lying between the curve and the horizontal axis, and, for each frequency band, the mean power observed in this frequency band during a given time frame is divided by the total power recorded during this time frame over the whole frequency interval. This is approximately equivalent to "normalizing" the measurement.

Figure 3:
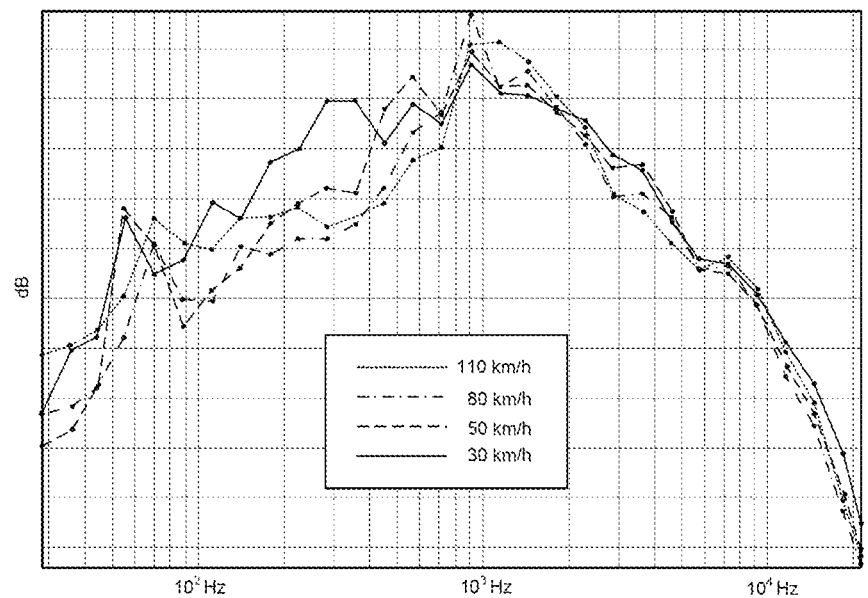
FIG. 3 shows the same power spectrum after normalizing.

It can then be seen in FIG. 3 that the curves obtained previously are substantially overlapping and have very similar profiles, particularly in the highest frequency bands and those most representative of the acoustic phenomena described above.

This normalization can be used to neutralize the effect related to speed, without substantially modifying the analytical capacity that can be derived from a sound recording during a specified time frame.

This advantage may prove to be decisive if it is not desired to connect the computer 2 to means for evaluating the vehicle speed, and if it is desired to obtain data on the condition of the road or vehicle in an independent manner.

For the sake of simplicity and speed of calculation, it may be considered that the total power is equal to the sum of the mean powers in each of the frequency bands of the frequency interval concerned.

Each of the points on the curve of FIG. 3 is a value representative of the mean acoustic power in a given frequency band. The set of these points can then form a vector in a vector space comprising a number of dimensions equal to the number of frequency bands. In the example used to illustrate the present description, a vector with 21 dimensions is obtained by considering a frequency interval segmented by thirds of an octave and lying within the frequency interval located between 200 Hz and 20 kHz. It should be noted in passing that the sum of the values forming the coordinates of a vector is equal to 1.

The choice of the frequency interval can also be adapted according to whether it is desired to completely eliminate the noise generated by the engine, the maximum amplitude of which is between 50 Hz and 60 Hz, in which case a frequency interval lying between 200 Hz and 20 kHz, for example, will be considered, or whether it is desired to retain the relevant portion of information contained in the frequency range below 200 Hz, in which case the spectrum over the whole interval from 0 Hz to 20 kHz will be taken into account.

The recording of the acoustic power during a time frame may be made on the basis of the sampling of the sound signal at a high frequency (around 40 kHz).

The implementation of the invention comprises a preliminary learning stage in which a large number of measurements is made while varying in a known way the modalities described above, which describe the meteorological condition, the road condition, the tire wear condition or the type of tread pattern of the tire. A vector found in the conditions described above is assigned to each of these measurements. Thus a vehicle-specific learning base is produced.

The methods of analysis and statistical processing of the data are known and do not form the subject of this invention. The linear discriminant analysis method which was used yielded reliable and robust results.

A first step of this method consists in determining the principal factor axes enabling the number of dimensions to be reduced to the number exactly necessary to describe the vectors assigned to each of the measurements along orthogonal axes. The change from the vector space where the number of dimensions is equal to the number of frequency bands, being typically 21 dimensions, to the reduced discriminant space is carried out by means of a linear transformation.

A second step then consists in using discriminant analysis properly so-called to find the areas in this reduced discriminant space containing the measurements made during the learning stage according to a given single modality or according to a combination of modalities.

The term "combination of modalities" is here taken to mean a condition representative of a given measurement made according to a modality chosen from each of the classes. By way of example, a measurement made in the "wet" condition on a "closed" road with a "worn" "summer" tire represents the combination of modalities "wet-closed-summer-worn". The number of combined modalities is therefore equal to the product of the number of modalities of each of the classes.

We then calculate, in this reduced discriminant space, the centre of gravity of the area containing the points representing a modality or a combination of modalities, together with a confidence interval representative of the dispersion of the points of a single area relative to this centre of gravity.

In the example used to illustrate the present description, the decrease in the number of dimensions between the initial discriminant space and the reduced discriminant space results in a change from 21 dimensions to about 15 dimensions. This small reduction indicates that it is taking the overall form of the spectrum into account that is characteristic of the expression of the different modalities. It also suggests that taking the powers of a reduced number of frequency bands into account does not emphasize any particular modality concerning the road or the tire, except for the modalities relating to the meteorological condition of the road.

Figure 4:
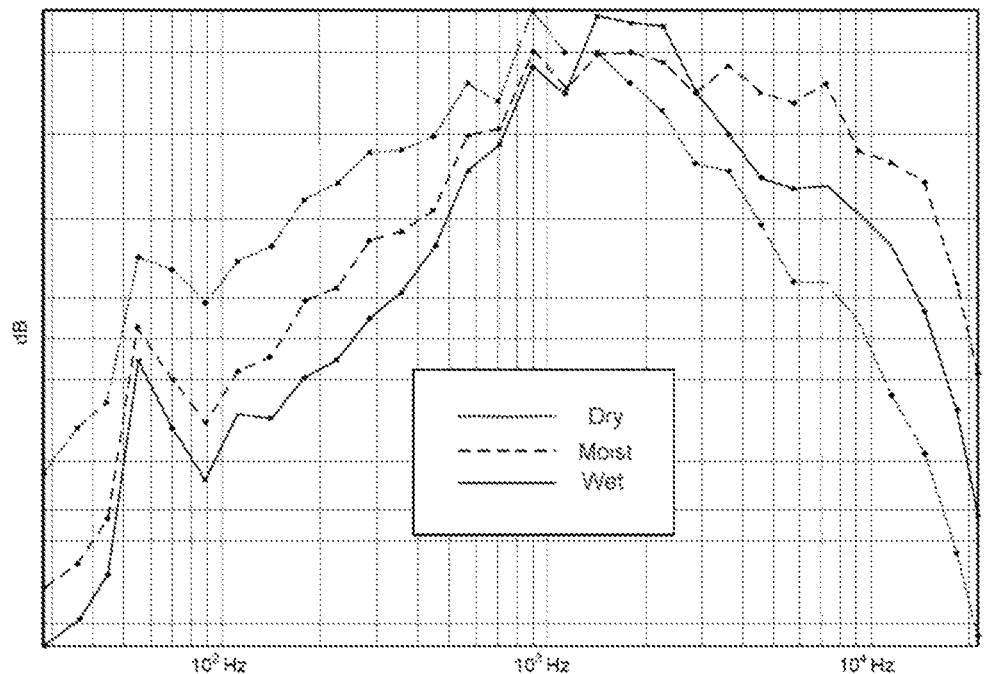
FIG. 4 shows the mean normalized power spectra for different meteorological conditions of the road.

FIG. 4 shows the spectral distribution of the "normalized" acoustic power, in frequency bands of ⅓ of an octave for three meteorological conditions of the road, all the other classes of modalities being equal.

Figure 5:
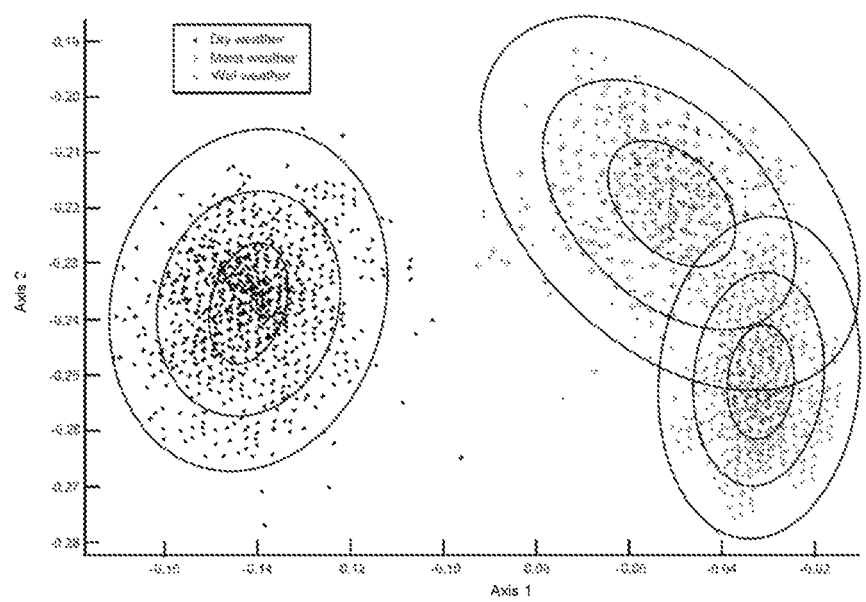
FIG. 5 shows a distribution of the measurements in a two-dimensional reduced discriminant space according to the meteorological condition of the road.

FIG. 5 shows, in a two-dimensional space, the distribution of the measurements according to one of the "dry", "moist" and "wet" modalities of the "weather" class for the road.

An initial observation makes it clear that the measurements made on dry ground do not overlap with the measurements made on moist or wet ground. A second observation reveals that the meteorological condition of the road can be determined independently of the other classes of modalities with a good degree of robustness.

The ellipses surrounding each of the clouds of points are placed at one, two and three standard deviations, and can be used to evaluate the dispersion of the measurements around the centre of gravity, and especially to assess the extent of coverage of one area with respect to another, which is representative of the risk of incorrectly assigning to another modality a measurement made according to a different given modality.

On the basis of these data, it is also possible to determine the probability that a new measurement will belong to one of the three modalities of the "weather" class for the road, by evaluating the distance from this point to the centre of gravity of each of these modalities.

Table 1 shows the probabilities of the classification of the meteorological condition of the road according to one of the three modalities "dry", "moist" and "wet".

TABLE 1

| Pj/i      | J = dry | J = moist | J = wet |
|-----------|---------|-----------|---------|
| i = dry   | 1       | 0         | 0       |
| i = moist | 0       | 0.91      | 0.09    |
| i = wet   | 0       | 0.03      | 0.97    |

As may be seen, sufficiently high probabilities are obtained to conclude that the vehicle is running on a "dry", "moist" or "wet" road. It is only the recognition of the "moist" modality that may be subject to incorrect attribution to the "wet" modality in 9% of cases.

Similarly, it would be possible to determine the condition of the road surface, with less robustness than the weather condition of the road, without needing to know the condition of the tire in advance. However, it is preferable to perform this analysis when the road is dry. This observation suggests that some acoustic phenomena related to the porosity and reflection of the ground are independent of the nature of the tire.

On the other hand, when similar analyses are performed, it is found that the areas containing the vectors relating to the modalities concerning the tire condition (wear or tread pattern) are relatively dispersed and interpenetrate to a considerable degree (with high dispersion around the centre of gravity and short distances between the centres of gravity), such that no conclusion can be drawn regarding a precise modality without a high risk of incorrect determination, particularly if the road condition is "moist" or "wet".

Thus, to ensure satisfactory robustness, the method provides for performing an initial analysis of the meteorological condition of the road and, if the vehicle is found to be running on a "dry" road, proceeding to a second analysis for discerning the modalities relating to the road surface, the tire wear condition and the type of tire tread pattern.

For greater robustness, it then appears preferable to perform the discriminant analysis by using the combined modalities of the three classes. The clouds of points representative of the vectors and the measurements made are then located in the reduced discriminant space according to a given combination of modalities chosen from each of the three modality classes "surface condition", "wear" and "tread pattern".

The modalities related to the tire tread pattern are denoted "A" for a "winter" tire and "P" for a "summer" tire; the modalities of the wear condition are denoted "N" for a "new" tire, "M" for a "half-worn" tire, and "U" for a "worn" tire; and finally the modalities of the surface condition are denoted "f" for the "closed" modality, "m" for the "medium" modality, and "o" for the "open" modality. The 18 combined modalities are then denoted, respectively: ANf, ANm, ANo, AMf, AMm, AMo, AUf, AUm, AUo, PNf, PNm, PNo, PMf, PMm, PMo, PUf, PUm, PUo.

Table 2 shows the probabilities found on the basis of the results of measurements contained in the learning base, for each of the 18 combinations of modalities. The dispersion of the measurements, observed for the modalities only, is then much smaller for the combined modalities and allows classification to be carried out much more efficiently.

TABLE 2

|     | ANf | ANm | ANo | AMf | AMm | AMo | AUf | AUm | AUo | PNf | PNm | PNo | PMf | PMm | PMo | PUf | PUm | PUo |
|-----|-----|-----|-----|-----|-----|-----|-----|-----|-----|-----|-----|-----|-----|-----|-----|-----|-----|-----|
| ANf | 0.9 | 0.02 |    | 0.03 |    |    | 0 |    |    |    |    |    |    |    |    |    |    |    |
| ANm |    | 0.99 |    |    | 0.01 |    |    |    |    |    |    |    |    |    |    |    |    |    |
| ANo |    |    | 0.96 |    |    |    |    |    |    |    |    | 0 |    |    |    |    |    |    |
| AMf |    |    |    | 0.95 |    |    | 0 |    |    |    |    |    | 0 |    |    |    |    |    |
| AMm |    | 0.01 |    |    | 0.95 |    |    | 0.01 |    |    |    |    |    | 0.01 |    |    | 0.03 |    |
| AMo |    | 0.03 |    |    |    | 0.96 |    |    |    |    |    |    |    |    |    |    |    |    |
| AUf |    |    |    |    |    |    | 1 |    |    |    |    |    |    |    |    |    |    |    |
| AUm |    |    |    | 0.01 |    |    |    | 0.97 |    |    |    |    |    | 0.01 |    |    | 0.01 |    |
| AUo |    |    |    |    |    |    |    |    | 0.91 |    |    |    |    |    |    |    |    | 0.1 |
| PNf |    |    |    |    |    |    | 0 |    |    | 1 |    |    |    |    |    | 0 |    |    |
| PNm |    | 0.01 |    |    |    |    |    |    |    |    | 0.97 |    |    | 0.02 |    |    |    |    |
| PNo |    |    |    |    |    |    |    |    |    |    |    | 1 |    |    |    |    |    |    |
| PMf |    |    |    |    |    |    |    |    |    |    |    |    | 1 |    |    | 0 |    |    |
| PMm |    | 0.01 |    |    | 0.02 |    |    |    |    |    | 0.01 |    |    | 0.96 |    |    |    |    |
| PMo |    |    |    |    |    |    |    |    |    |    |    |    |    |    | 1 |    |    |    |
| PUf |    |    |    |    |    |    |    |    |    |    |    | 0 |    |    |    | 1 |    |    |
| PUm |    |    |    |    |    |    |    | 0.06 |    |    |    |    |    | 0.03 |    |    | 0.91 |    |
| PUo |    |    |    |    |    | 0.03 |    |    | 0.1 |    |    |    |    |    |    |    |    | 0.9 |

The overall probability of detection of one of the combinations of modalities is about 0.96.

The next step is to recognize, for a given new measurement, the modality of each of the classes "surface condition", "wear", and "tread pattern" in which the measurement was made.

Table 3 can be used to determine the probabilities of detection of the modality of one of the three classes as a function of the combinations of modalities.

Table 3 indicates that, if a measurement is assigned to the class "AUf" (Winter, Worn, closed surface), it is possible to have high confidence in the determination of the tread pattern (1), the wear condition (U), and the surface condition (1). A relatively lower degree of confidence is found in the class "AUo" (Winter, Worn, open) for which the prediction concerning the type of tire tread pattern is less good (0.91).

TABLE 3

| Class found | Probability of detection of the class | | |
|---|---|---|---|
|   | Thread pattern | Wear | Surface |
| ANf | 1 | 0.95 | 0.98 |
| ANm | 1 | 0.99 | 1 |
| ANo | 0.96 | 1 | 1 |
| AMf | 0.98 | 0.95 | 1 |
| AMm | 0.97 | 0.96 | 1 |
| AMo | 0.99 | 0.96 | 0.99 |
| AUf | 1 | 1 | 1 |
| AUm | 0.98 | 0.98 | 1 |
| AUo | 0.91 | 1 | 1 |
| PNf | 0.98 | 0.95 | 1 |
| PNm | 0.99 | 0.98 | 1 |
| PNo | 1 | 1 | 1 |
| PMf | 1 | 0.97 | 1 |
| PMm | 0.97 | 0.98 | 1 |
| PMo | 1 | 1 | 1 |
| PUf | 1 | 0.97 | 1 |
| PUm | 0.94 | 0.97 | 1 |
| PUo | 0.87 | 0.97 | 1 |

The learning base is used to locate the areas in which the combined modalities are situated in the reduced discriminant space, together with their centres of gravity and their dispersion. Typically, in the case of the present description, the 18 areas of the 18 combined modalities in question are located in the reduced discriminant space.

Then, on the basis of the location of the vector associated with each new measurement and transformed in the reduced vector space, a probability is determined, for each of the modalities of a class, for each of the combinations of modalities containing this modality, and the modality of the class having the highest probability is attributed to this measurement.

Thus, if the weather class that is found is "dry", the 21 variables of the vector obtained from the measurement can be used, by means of the discriminant analysis based on the learning base, to determine a probability of belonging to one of the combined modalities according to the "surface condition" class, the "wear" class or the "tread pattern" class, or, typically, in the case used to illustrate the present description, the probability of belonging to one of the 18 classes of combined modalities: ANf, ANm, ANo, AMf, AMm, AMo, AUf, AUm, AUo, PNf, PNm, PNo, PMf, PMm, PMo, PUf, PUm, PUo. This probability is calculated, for example, by evaluating a distance from the centre of gravity of the combined modality class in question.

The probability that the measurement belongs to one of the modalities of a particular class, other than the weather class, is then found by a second probability calculation, called the "tread pattern+wear+surface on dry ground" model, in the following manner.

The probability of the "closed" road condition modality is deduced from the relation p(surface="closed")= p ("closed")=p(ANf)+p(AMf)+p(AUf)+p(PNf)+p(PMf)+p(PUf)

Similarly, we deduce:

p(surface="medium")=p("medium")=p(ANm)+p(AMm)+p(AUm)+p(PNm)+p(PMm)+p(PUm), and p(surface="open")=p("open")=p(ANo)+p(AMo)+p(AUo)+p(PNo)+p(PMo)+p(PUo).

We then find the one of the three probabilities that is maximum and gives the modality of the detected surface condition and the associated probability:

p(surface)=max [p("closed"), p("medium"), p("open")].

Similarly, p(tread pattern=max [p("Winter"), p("Summer")], where:

p(tread pattern="Winter")=p("Winter")=p(ANf)+p(ANm)+p(ANo)+p(AMf)+p(AMm)+p(AMo)+p(AUf)+p(AUm)+p(AUo) and p(tread pattern="Summer")=p("Summer")=p(PNf)+p(PNm)+p(PNo)+p(PMf)+p(PMm)+p(PMo)+p(PUf)+p(PUo).

Finally, the wear is given by p(wear=max [p("new"), p("half-worn"), p("worn")], where:
p(wear="new")=p ("new")=p(ANf)+p(ANm)+p(ANo)+p(PNf)+p(PNm)+p(PNo), p(wear="half-worn")=p("half-worn")=p(AMf)+p(AMm)+p(AMo)+p(PMf)+p(PMm)+p(PMo), and
p(wear="worn")=p ("worn")=p(AUf)+p(AUm)+p(AUo)+p(PUf)+p(PUm)+p(PUo).

The probability of assignment to a modality based on a given measurement is then compared with a specified threshold, in order to decide on the validity of the result and its transmission to a display system or a driver assistance system. By way of example, all detections whose probability of classification is not at least 0.75 are rejected. And if this probability is between 0.95 and 0.75, the result based on the measurement must be confirmed by one or more subsequent measurements.

It should be noted here that, unlike the meteorological condition or the surface condition of the road which may change abruptly and require rapid decision-making, the variations of the wear or the tire tread pattern type are factors that are much more stable in time, typically over time scales corresponding to travel over distances of 100 or even 1000 kilometers. However, since the detection of these tire parameters depends on the road condition, the paradoxical outcome is that they need to be detected almost as rapidly as the road condition.

The probability of incorrect determination on these two criteria can be greatly reduced by cumulating the observations made using a plurality of consecutive measurements, before deciding on the actual wear condition or the type of tread pattern of the tire fitted to the vehicle.

Figure 6:
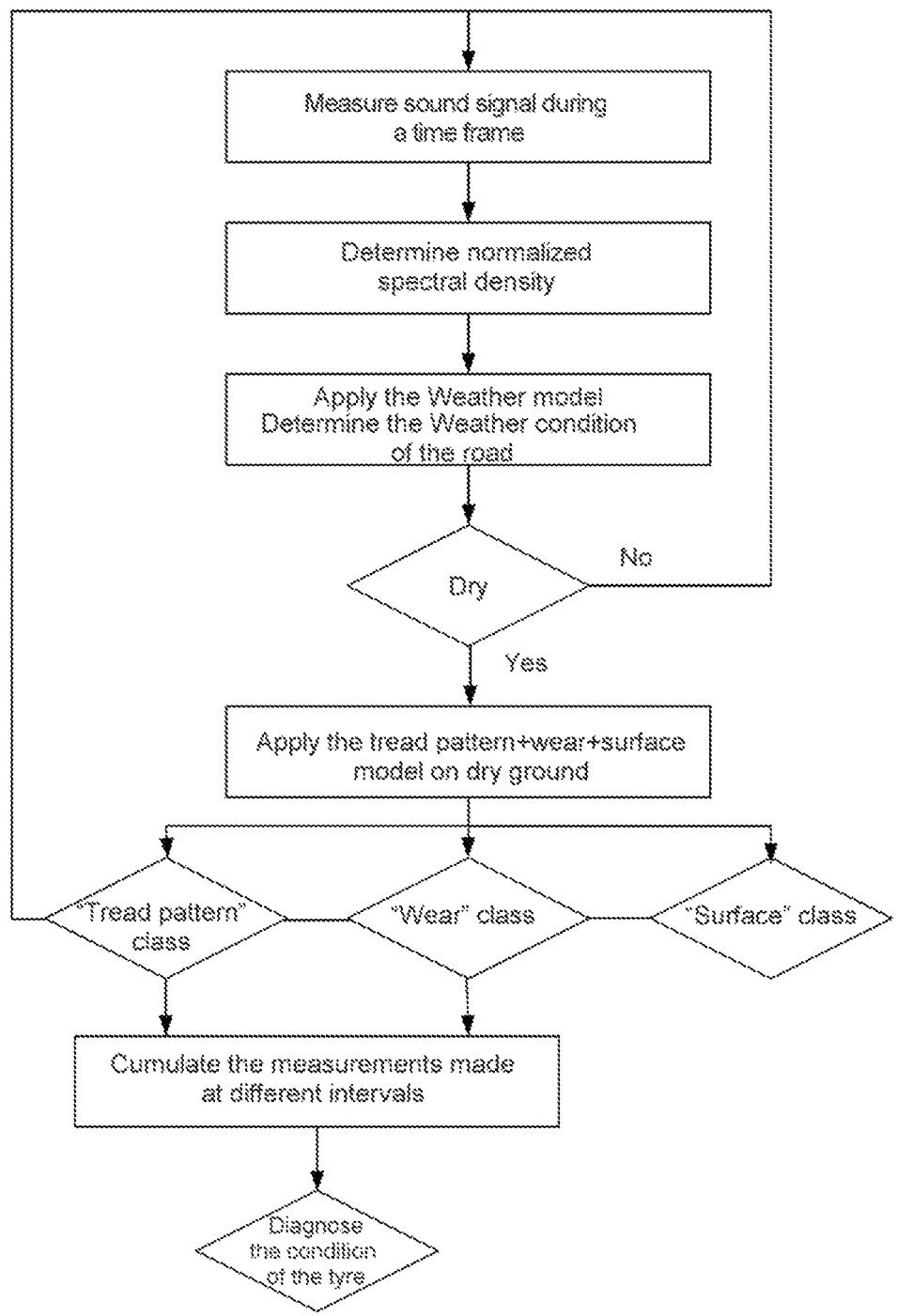
FIG. 6 shows a functional block diagram of the steps of execution of the method according to the invention.

FIG. 6 shows the sequence of operations performed in the method according to the invention.

After the frequency spectrum of the acoustic power has been measured in a given time frame, typically ¼ of a second, the spectrum is divided into bands of known width, typically ⅓ of an octave, over a given frequency interval, typically from 200 Hz to 20 kHz. The sampling of the measurement, during the 0.25 second time frame, is performed at a frequency of 44100 kHz.

A linear transformation is used to transfer the normalized vector resulting from the measurement from the 21-dimensional space to a reduced discriminant space. The meteorological condition of the road is then determined directly, and, if the road is found to be in the "dry" modality, the probabilities of association of the measurement with each of the combined modalities are determined, and the tire tread pattern type, the tire wear and the road surface condition are then deduced from these by using the "tread pattern+wear+surface on dry ground" model.

The cumulative result relating to the tire condition can then be determined with a good degree of robustness by cumulating the results of the measurements made at regular time intervals, for the purpose of transmitting a diagnosis of the tire condition and the road condition to a display means or to a driver assistance system or to a road condition monitoring unit.

The invention therefore makes it possible to determine, in a robust manner and on the basis of a single sound intensity measurement made during a short time frame, the meteorological condition of the road as well as, more unexpectedly, the condition of the road surface or of the tire, without any need to know the speed of the vehicle.

The embodiments of the invention on which the present description is based are not limiting, and may be varied as regards their implementation, in particular in terms of the choice of the methods of numerical data analysis, provided that they enable the technical effects to be obtained as described and claimed.

The invention claimed is:

1. A method, implemented using a system comprising a microphone and a computer, of determining a condition of a road and a condition of a tire fitted on a vehicle travelling on the road, the method comprising steps of:
   using the microphone to measure a sound signal produced by the tire running on a surface of the road during a given time frame, and recording the measurement; and
   using the computer, which is connected to the microphone, to execute operations comprising:
   (1) determining a spectral density of a power of the sound signal over a given frequency interval;
   (2) segmenting the given frequency interval into a plurality of frequency bands of pre-determined width, each frequency band being associated with a representative data element representing a mean acoustic power measured in that frequency band, wherein the representative data elements obtained from the measurement form variables of a vector associated with the measurement; and
   (3) determining a road condition and a tire condition corresponding to the vector associated with the measurement by analyzing the representative data elements using a discriminant-analysis technique and using a learning base, stored in a storage of the computer, that includes a set of vectors associated with previously recorded measurements made by the steps of the method, in known running conditions, according to modalities that each represent a given road condition or a given tire condition,
   wherein each of the representative data elements forming the variables of the vector associated with the measurement is obtained by the computer by finding a ratio between (a) the mean acoustic power measured in the frequency band corresponding to the representative data element and (b) a total acoustic power measured over a whole of the given frequency interval.

2. The method according to claim 1, wherein the total acoustic power is equal to a sum of the mean acoustic powers of all the frequency bands of the given frequency interval.

3. The method according to claim 1, wherein the frequency bands are determined by dividing the given frequency interval into thirds of an octave.

4. The method according to claim 1, wherein the given time frame of the measurement is less than or equal to 0.5 seconds.

5. The method according to claim 1, wherein the given frequency interval is in a range of from 0 Hz to 20 kHz.

6. The method according to claim 1, wherein the given frequency interval is in a range of from 200 Hz to 20 kHz.

7. The method according to claim 1, wherein the modalities include a weather-condition class of modalities representing different meteorological road conditions, the weather-condition class of modalities including: a dry condition modality, a moist condition modality, and a wet condition modality.

8. The method according to claim 1, wherein the modalities include a surface-condition class of modalities representing different conditions of a surface of the road, the surface-condition class of modalities including: a closed condition modality (f), a medium condition modality (m), and an open condition modality (o).

9. The method according to claim 1, wherein the modalities include a wear-condition class of modalities representing different conditions of wear of the tire, the wear-condition class of modalities including: a new condition modality (N), a half-worn condition modality (M), and a worn condition modality (U).

10. The method according to claim 1, wherein the modalities include a tread-type class of modalities representing different types of tread patterns of the tire, the tread-type modalities including: a summer pattern modality (P), and a winter pattern modality (A).

11. The method according to claim 1, wherein the discriminant analysis technique used to analyze the representative data elements includes steps of:
    determining a reduced discriminant space using the learning base, and, for each modality of a group of modalities and for each combination of a group of combinations of modalities, identifying in the reduced discriminant space an area encompassing the modality or the combination,
    transforming the vector associated with the measurement to the reduced discriminant space, and, based on a location of the vector in the reduced discriminant space, associating the measurement with a probability of each modality of the group of modalities and each combination of the group of combinations of modalities, and
    determining a most probable modality for each of a plurality of classes of modalities,
    wherein the classes of modalities include: a weather-condition class, a surface-condition class, a wear-condition class, and a tread-pattern class,
    wherein the group of modalities include: dry road, moist road, wet road, closed surface (f), open surface (o), medium surface (m), worn tire (U), half-worn tire (M), new tire (N), summer tread (P), winter tread (A), and
    wherein the group of combinations of modalities include: ANf, ANm, ANo, AMf, AMm, AMo, AUf, AUm, AUo, PNf, PNm, PNo, PMf, PMm, PMo, PUf, PUm, and PUo.

12. The method according to claim 11, wherein, after a determination is made that the measurement was made on a dry road, a modality belonging to the surface-condition class or the wear-condition class or the tread-pattern class is associated with the measurement.

13. The method according to claim 12, wherein:
    for each modality of a class of modalities, a probability is associated with the measurement according to each combination of modalities containing the modality, and
    a modality of a class of modalities having a highest probability is attributed to the measurement.

14. The method according to claim 13, wherein a diagnosis of a condition of the tire is made according to a modality in the wear-condition class of modalities or the tread-pattern class of modalities, by combining results of measurements made at different time intervals.

15. The method according to claim 1, wherein the microphone is positioned in a front part of a wheel housing located at a rear section of the vehicle.

* * * * *

UNITED STATES PATENT AND TRADEMARK OFFICE
CERTIFICATE OF CORRECTION

PATENT NO. : 10,365,248 B2  
APPLICATION NO. : 15/103987  
DATED : July 30, 2019  
INVENTOR(S) : Antoine Paturle et al.

Page 1 of 1

It is certified that error appears in the above-identified patent and that said Letters Patent is hereby corrected as shown below:

On the Title Page

Item (71) (Applicants):
"Antoine Paturle, Clermont-ferrand (FR);Jerôme Antoni, Clermont-ferrand (FR)" should read
--COMPAGNIE GENERALE DES ETABLISSMENTS MICHELIN, Clermont-Ferrand (FR);
Michelin Recherche et Technique S.A., Granges-Paccot (CH)--.

Signed and Sealed this  
Eleventh Day of February, 2020

Andrei Iancu  
*Director of the United States Patent and Trademark Office*